US012693288B2

(12) United States Patent
Okumura et al.

(10) Patent No.: US 12,693,288 B2
(45) Date of Patent: Jul. 28, 2026

(54) QUALITY CONTROL SUBSTANCE FOR USE IN THE ANALYSIS OF ERYTHROCYTES

(71) Applicant: ARKRAY, Inc., Kyoto (JP)

(72) Inventors: Kazuko Okumura, Kyoto (JP); Atsushi Nakao, Kyoto (JP); Kazuki Kudo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 390 days.

(21) Appl. No.: 18/468,590

(22) Filed: Sep. 15, 2023

(65) Prior Publication Data

US 2024/0094192 A1     Mar. 21, 2024

(30) Foreign Application Priority Data

Sep. 16, 2022     (JP) ................................. 2022-148425

(51) Int. Cl.
| | |
|---|---|
| *G01N 33/493* | (2006.01) |
| *G01N 15/01* | (2024.01) |
| *G01N 15/06* | (2024.01) |
| *G01N 15/075* | (2024.01) |

(52) U.S. Cl.
CPC ........... *G01N 33/493* (2013.01); *G01N 15/06* (2013.01); *G01N 15/01* (2024.01); *G01N 15/075* (2024.01)

(58) Field of Classification Search
None
See application file for complete search history.

(56) References Cited

U.S. PATENT DOCUMENTS

| | | | |
|---|---|---|---|
| 2019/0101742 A1 | 4/2019 | Nakajima et al. |
| 2020/0371086 A1 | 11/2020 | Das |
| 2023/0047416 A1 | 2/2023 | Umberger et al. |

FOREIGN PATENT DOCUMENTS

| | | | |
|---|---|---|---|
| CN | 105860080 | * | 8/2016 |
| JP | 2007-178315 | A | 7/2007 |
| JP | 2019-066461 | A | 4/2019 |
| JP | 2020-531852 | A | 11/2020 |
| WO | 2021/127424 | A1 | 6/2021 |

OTHER PUBLICATIONS

IWASE COSFA, Raspberry shaped silicone powder "NH-RAS06" (Year: 2015).*
Miranda et al., Properties and Applications of PDMS for Biomedical Engineering: A Review, Funct. Biomater. 2022, 13, 2. https://doi.org/10.3390/jfb13010002, 2022 (Year: 2022).*
Communication pursuant to Article 94(3) EPC issued by the European Patent Office on Jul. 30, 2025, which corresponds to European Patent Application No. 23 197 665.5-1001 and is related to U.S. Appl. No. 18/468,590.
Nobuko Imai et al. "Preparation and utility of control urine for urinary sediment examination" Hygiene Examination, 1990, pp. 55-61, vol. 39, Issue 1.
The extended European search report issued by the European Patent Office on Jan. 29, 2024, which corresponds to European Patent Application No. No. 23197665.5-1001 and is related to U.S. Appl. No. 18/468,590.
Chien et al., "Urine sediment examination: A comparison of automated urinalysis systems and manual microscopy", Clinica Chimica Acta, vol. 384, No. 1, May 26, 2007, pp. 28-34.
An Office Action mailed by the Japanese Patent Office on Mar. 31, 2026, which corresponds to Japanese Patent Application No. 2022-148425 and is related to U.S. Appl. No. 18/468,590; with English language translation.

* cited by examiner

*Primary Examiner* — Robert A Wax

(74) *Attorney, Agent, or Firm* — Studebaker Brackett PLLC

(57)     ABSTRACT

The present disclosure provides a quality control substance for use in the analysis of erythrocytes, which can be prepared safely with easily available raw materials, which has an excellent preservation stability, and which can be used in the analysis of sediments in a sample. This quality control substance includes artificial particles whose form as observed with a microscope is similar to the form of erythrocytes as observed therewith.

6 Claims, 13 Drawing Sheets

QUALITY CONTROL SUBSTANCE FOR USE IN THE ANALYSIS OF ERYTHROCYTES

TECHNICAL FIELD

The present disclosure relates to a quality control substance which is used for quality control in the analysis of sediments in a sample. More particularly, the present disclosure relates to a quality control substance to be used in the analysis of erythrocyte items.

BACKGROUND ART

Examinations have been performed in which a disease of a patient is diagnosed by observing sediments contained in a sample, such as urine or blood, collected from the patient with a microscope, identifying erythrocytes among the thus observed sediments and counting the number thereof. For example, if the erythrocyte count is higher than a reference value, in urine sediment examination in which the types of the sediments contained in urine are identified, and the concentration of each sediment is measured, nephritis or the like is suspected. The examination of sediments using a microscope is performed by a method such as microscopy in which a laboratory technician directly observes a sample and counts the number of sediments, a method in which an automatic analyzer mounted on a microscope is used to identify the types of sediments, and to count the number of the sediments, or the like. In any of the cases of counting the number of erythrocytes in a sample by such a method, quality control is necessary in order to accurately detect and identify erythrocytes based on the forms of the sediments.

Non-patent Document 1 discloses a control urine for urine sediment analysis, which includes erythrocytes and leukocytes separated from human-derived blood and immobilized with glutaraldehyde, as a quality control substance intended for use in quality control.

Patent Document 1 discloses a quality control substance which includes: a cancer cell as a substance that indicates the form of a non-squamous epithelial cell in urine; an algae cell as a substance that indicates the form of an abnormal cast in urine; a yeast cell as a substance that indicates the form of a yeast cell in urine; and egg white as a substance that indicates the form of mucus in urine. In other words, an object of the technique disclosed in Patent Document 1 is to perform quality control, in the case of observing a urine sample with a microscope, by using other substances whose forms are similar to urine sediments in the urine sample, and comparing the forms of components in the quality control substance with the forms of components in the urine sample.

PRIOR ART DOCUMENTS

Patent Documents

[Patent Document 1] JP2020-531852A
[Patent Document 2] JP2019-66461A

Non-Patent Documents

[Non-patent Document 1] Nobuko Imai et al., "Preparation and utility of control urine for urinary sediment examination", Hygiene Examination, Vol. 39, Issue 1, 1990, p. 55 to 61.

SUMMARY OF THE INVENTION

In the case of preparing a quality control substance containing erythrocytes, such as one disclosed in Patent Document 1, the difficulty to obtain erythrocytes due to ethical reasons has been a problem. Further, since components derived from living bodies are unstable and infectious, the handling of such components requires certain skills, which has also been a problem.

In view of such circumstances, an object of the present disclosure is to provide a quality control substance for use in the analysis of erythrocytes (namely, a quality control substance for controlling the measurement accuracy for measuring a concentration of erythrocytes), which can be prepared safely with easily available raw materials, which has an excellent preservation stability, and which can be used in the analysis of sediments in a sample.

The present inventors have found out that the form of a specific type of artificial particle is similar to the form of erythrocytes in a sample, when observed with a microscope, and that the artificial particles can be suitably used as a quality control substance for use in the analysis of erythrocytes, in the analysis of sediments in the sample, thereby completing the present disclosure.

Specifically, the present disclosure provides the following:

[1] A method for analyzing a sample using a urine sediment analyzer, comprising the steps of:
controlling the measurement accuracy of the urine sediment analyzer with artificial particles whose form as observed with a microscope is similar to the form of erythrocytes as observed therewith, for measuring a concentration of erythrocytes in the sample; and
analyzing the sample with the urine sediment analyzer.

[2] The method according to [1], wherein the artificial particles have a spherical form, an approximate spherical form, a golf ball-like form or a raspberry-like form.

[3] The method according to [1] or [2], wherein the artificial particles have an average particle size of from 2 μm to 6 μm.

[4] The method according to any one of [1] to [3], wherein the artificial particles are made of a silicone-based polymer.

[5] The method according to [4], wherein the silicone-based polymer is polymethylsilsesquioxane.

[6] The method according to any one of [1] to [5], wherein the color of the artificial particles as observed with the microscope is similar to the color of the erythrocytes as observed therewith.

[7] The method according to any one of [1] to [6], wherein the artificial particles are artificial particles included in at least one of NH-RAS06 (manufactured by Nikko Rica Corporation) or Twinone SS-1000 (manufactured by CQV CO., Ltd.).

[8] A method for controlling a measurement accuracy of an analyzer that measures a concentration of particles whose form is similar to the form of erythrocytes in a sample, by counting the number of the particles in the sample, the method comprising the steps of:
measuring a concentration of particles in a quality control substance comprising artificial particles whose form is similar to the form of erythrocytes, using the analyzer, to obtain a measured value; and
determining the measurement accuracy of the analyzer by comparing the measured value with a reference value.

[9] The method according to [8], wherein the artificial particles have a spherical form, an approximate spherical form, a golf ball-like form or a raspberry-like form.

[10] The method according to [8] or [9], wherein the artificial particles have an average particle size of from 2 μm to 6 μm.

[11] The method according to any one of [8] to [10], wherein the artificial particles are made of a silicone-based polymer.

[12] The method according to [11], wherein the silicone-based polymer is polymethylsilsesquioxane.

[13] The method according to any one of [8] to [12], wherein the color of the artificial particles as observed with the microscope is similar to the color of the erythrocytes as observed therewith.

[14] The method according to any one of [8] to [13], wherein the artificial particles are artificial particles included in at least one of NH-RAS06 (manufactured by Nikko Rica Corporation) or Twinone SS-1000 (manufactured by CQV CO., Ltd.).

Effect of the Invention

Since the artificial particles included in the quality control substance according to the present disclosure have a high preservation stability, it is possible to perform quality control in a preferred manner, in the case of analyzing erythrocytes which can be present in a sample using the quality control substance according to the present disclosure. Further, since the quality control substance for use in the analysis of erythrocytes according to the present disclosure can be prepared safely without ethical problems, it is possible to expect improvements in operability at production sites and convenience at clinical sites. In addition, the use of a commercially available product of artificial particles enables to obtain a large amount of a quality control substance having the same quality. Artificial particles are preferred from the viewpoint that they can be obtained and used without any ethical problem due to being industrial products, that they have an excellent preservation stability, and that they can be used safely due to not being infectious.

EMBODIMENTS FOR CARRYING OUT THE INVENTION

<Quality Control Substance>

Figure 1:
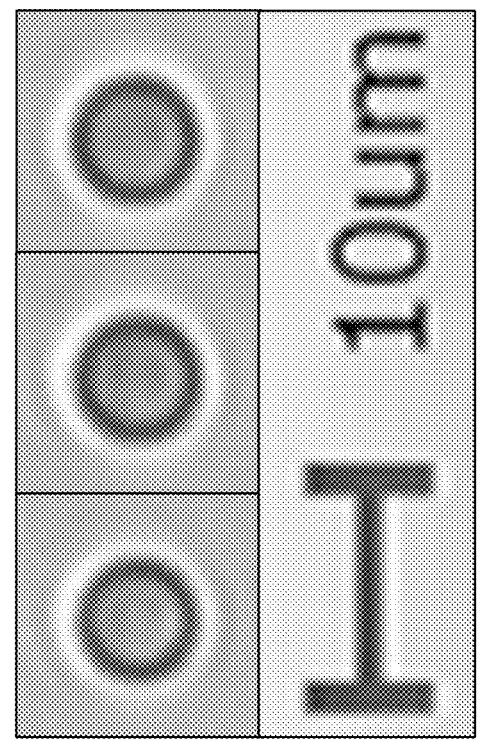
FIG. 1 shows images (photographs) illustrating the form of the particles of NH-RAS06 contained in Sample 1, captured by a urine sediment analyzer.

One embodiment of the present disclosure is a quality control substance which is for use in a sediment analysis with a microscope, and which includes artificial particles whose form as observed with the microscope is similar to the form of erythrocytes as observed therewith. In the present specification, the microscope to be used is preferably a light microscope.

The quality control substance according to the present embodiment is preferably a quality control substance for use in a urine sediment analyzer, particularly, a urine sediment analyzer based on a microscope, and is a quality control substance for controlling the measurement accuracy for measuring a concentration of erythrocytes in a sample. The quality control substance according to the present embodiment is also preferably a quality control substance which is used by a laboratory technician, for observing erythrocytes in a sample with a microscope to count the number of erythrocytes in the sample, and is also a quality control substance for controlling the measurement accuracy for measuring the concentration of the erythrocytes in the sample.

The definition of the quality control substance includes a quality control substance used for the quality control of a urine sediment analyzer based on a microscope, in the analysis of erythrocyte items. The quality control substance includes artificial particles whose form as observed with a microscope is similar to the form of erythrocytes as observed therewith. In other words, the quality control substance includes such artificial particles that an image similar to the image obtained by observing an individual erythrocyte with a microscope can be obtained by observing an individual artificial particle with the microscope.

The definition of the quality control substance includes a quality control substance which is used for controlling the measurement accuracy in the case of counting the number of particles indicating the form of erythrocytes, in a sample, and measuring the erythrocyte concentration in the sample, based on the counted value. The definition of the expression "counting the number of particles indicating the form of erythrocytes, in a sample" includes: a situation in which a laboratory technician observes and counts the number of such particles in the sample with a microscope; and a situation in which an analyzer including a microscope and a camera is used to capture particles in the sample by the camera via the microscope, to acquire an image in which the particles in the sample are captured, and the number of particles indicating the form of erythrocytes, among the particles captured in the acquired image, is automatically counted by the analyzer. The concentration of the particles in a sample may be measured based on the counted value of the particles contained in a predetermined amount of the sample. Alternatively, it is possible to obtain a correlation between the number of particles observed within the range of a predetermined visual field of a microscope and the particle concentration in a sample, in advance; count the number of particles observed within the range of the pre-determined visual field of the microscope, and measure the particle concentration from the counted value and the cor-relation.

The artificial particles included in the quality control substance preferably include artificial particles whose form as observed with a microscope is similar to the form of erythrocytes as observed therewith. Examples of the form of the artificial particles whose form is similar to the form of erythrocytes when observed with a microscope, include a spherical form, an approximate spherical form, a golf ball-like form (a spherical shape with concave portions on the surface thereof), a raspberry-like form (a spherical shape with protrusions on the surface thereof) and a polyhedral form.

The artificial particles included in the quality control substance can have an average particle size of from 2 μm to 13 μm, and preferably from 2 μm to 6 μm. In cases where the artificial particles do not have a spherical form, the particle size of each artificial particle is defined by the diameter of its circumscribed sphere.

Examples of the material of the artificial particles included in the quality control substance include synthetic polymers, semisynthetic polymers and natural polymers. Of these, synthetic polymers are preferred. Examples of the synthetic polymers include silicone-based polymers (such as polymethylsilsesquioxane and (dimethicone/vinyl dimethi-cone) crosspolymers), acrylic polymers (such as polymethyl methacrylate) and styrene-based polymers (such as polysty-rene and styrene-acrylonitrile copolymers). Of these, a sili-cone-based polymer is preferred.

More specifically, it is preferred to use, as the quality control substance, particles made of polymethylsilsesqui-oxane, commercially available under the names of NH-RAS06 (raspberry-like, alumina microparticle-encapsulated polymethylsilsesquioxane particles, manufactured by Nikko Rica Corporation) and Twinone SS-1000 (golf ball-like polymethylsilsesquioxane particles, manufactured by CQV CO., Ltd.), which include particles whose form is similar to the form of erythrocytes.

The silicone-based polymer in the present disclosure is not particularly limited, as long as the polymer has a (poly)siloxane structure in the molecular chain. The sili-cone-based polymer may be a homopolymer (monopoly-mer) of a compound having a (poly)siloxane structural unit, or may be a copolymer of a compound having a (poly)siloxane structural unit and another compound, namely, a copolymer having a (poly)siloxane structural unit and another structural unit. The other compound is a non-siloxane-based monomer or polymer, and the other struc-tural unit is a non-siloxane-based structural unit.

In addition, examples of the material of the artificial particles include metals; oxides, nitrides, fluorides, sulfides and borides of metals; complex compounds thereof, and hydroxyapatite.

The color of the artificial particles included in the quality control substance as observed with the microscope is pref-erably similar to the color of erythrocytes as observed therewith.

Examples of the structure of the artificial particles included in the quality control substance include a non-porous structure and a porous structure. Of these, a non-porous structure is preferred.

The quality control substance according to the present embodiment may include an aqueous solvent as long as the effects of the present disclosure are not impaired. Examples of the aqueous solvent include water and phosphate buffered saline (PBS).

The quality control substance according to the present embodiment may further include an additional component as long as the effects of the present disclosure are not impaired. Examples of the additional component include a surfactant, an ionic substance and a water-soluble polymer. The sur-factant may be, for example, polyoxyethylene (20) sorbitan monolaurate (such as one commercially available under the name of Tween® 20).

<Method for Controlling Measurement Accuracy>

Another embodiment of the present disclosure is a method for controlling a measurement accuracy of an analyzer that measures a concentration of particles whose form is similar to the form of erythrocytes in a sample, by counting the number of the particles in the sample, the method including the steps of:

measuring the concentration of the particles in the quality control substance described in the section of <Quality Control Substance>, using the analyzer, to obtain a measured value; and determining the measurement accuracy of the analyzer by comparing the measured value with a reference value.

The "concentration of particles" refers to the number of particles contained in a unit volume, which is also referred to as "number concentration".

The analyzer is, for example, an analyzer that includes a microscope, and a camera for imaging particles in a sample. The analyzer acquires an image in which the particles in the sample are captured, by imaging the particles in the sample with the camera via the microscope; counts the number of particles (similar particles) which are captured in the acquired image and whose degree of similarity with the form of erythrocyte particles stored in the analyzer in advance is equal to or higher than a predetermined value, as erythro-cytes; and measure the concentration of the similar particles in the sample as the erythrocyte concentration, based on the counted value. The analyzer that measures the erythrocyte concentration in a sample may be, for example, a urine sediment analyzer based on a microscope, and the urine sediment analyzer based on a microscope may be, for example, AUTION EYE® AI-4510 (manufactured by Arkray, Inc.).

The sample is not particularly limited as long as the sample possibly contains erythrocytes. Examples of the sample include urine and blood. Of these, urine is preferred.

When the quality control substance is analyzed using the analyzer, the artificial particles whose form as observed with a microscope is similar to the form of erythrocytes as observed therewith, included in the quality control sub-stance, are counted as the similar particles (erythrocytes), and the concentration of the artificial particles included in the quality control substance is measured as the concentra-tion of the similar particles (concentration of erythrocytes). The measurement accuracy of the analyzer may be deter-mined by comparing the thus measured value of the con-centration of the artificial particles with a reference value, and based, for example, on the difference between the measured value of the concentration of the artificial particles and the reference value. In this case, the analyzer can be determined to have a good measurement accuracy, if the difference is less than a predetermined value. On the other hand, the analyzer can be determined to have a poor measurement accuracy, if the difference is equal to or higher than the predetermined value. Alternatively, the measurement accuracy of the analyzer may be determined based on the proportion of the measured value of the concentration of the artificial particles with respect to the reference value. In this case, the analyzer can be determined to have a good measurement accuracy, if the proportion is less than a predetermined value. On the other hand, the analyzer can be determined to have a poor measurement accuracy, if the proportion is equal to or higher than the predetermined value. The predetermined value can be set as appropriate depending on the accuracy required for the analyzer.

The reference value can be, for example: the value obtained by analyzing the same quality control substance with a plurality of analyzers to obtain a plurality of measured values of the concentration of the similar particles, and averaging the thus obtained measured values; the measured value of the concentration of the similar particles obtained by measuring the quality control substance by microscopy; the measured value of the concentration of the similar particles (measured value of the concentration of erythrocytes) obtained by measuring the quality control substance with a quality-controlled analyzer; or the like. The reference value can also be the mean value of the concentrations of the similar particles (concentrations of erythrocytes) which have been measured by analyzing the quality control substance multiple times, in advance, with the above-described analyzer.

<Method for Detecting Erythrocytes in Sample>

Another embodiment of the present disclosure is a method for detecting the presence of erythrocytes in a sample derived from a subject, the method including the steps of:

analyzing the quality control substance described in the section of <Quality Control Substance> described above, using a urine sediment analyzer, in order to determine the form of the artificial particles in the quality control substance;

analyzing the sample derived from the subject and containing sediments, using the urine sediment analyzer;

comparing the form of the artificial particles in the quality control substance with the forms of the sediments in the sample; and determining the presence of erythrocytes in the sample, if any of the forms of the sediments in the sample matches the form of the artificial particles in the quality control substance.

The "subject" refers to an individual who undergoes the examination of sediments in a sample derived from the individual. The subject may be an individual with a disease, an individual suspected to have a disease, or a healthy individual. The subject is preferably a human being.

The sample is not particularly limited as long as the sample possibly contains erythrocytes. Examples of the sample include urine and blood. Of these, urine is preferred.

Whether or not the form of erythrocytes in the sample matches the form of the artificial particles in the quality control substance can be automatically determined by the urine sediment analyzer to be used. For example, in the case of using the urine sediment analyzer disclosed in Patent Document 2, which is based on an unstained image analysis performed in a fluid, the analyzer that identifies the types of sediments extracts the feature values (such as color, form and particle size) of the artificial particles in the quality control substance from the images of the artificial particles, and stores the feature values thereof as the feature values of erythrocytes in the urine sediment analyzer, in advance. In the case of automatically identifying the sediments in the sample, the above-described analyzer extracts the feature values of the respective sediments in the sample from the images of the sediments; performs a pattern matching with the feature values of erythrocytes, which had been stored in the urine sediment analyzer in advance, to determine whether or not any of the forms of the sediments matches the form of erythrocytes (namely, whether or not the degree of similarity between the forms of both is equal to or higher than a certain value); and indicates the presence of erythrocytes in the sample, if it is determined that the forms of both match with each other.

Further, the urine sediment analyzer may count the number of erythrocytes detected.

The definition of the urine sediment analyzer includes a urine sediment analyzer based on a microscope. The urine sediment analyzer based on a microscope may be, for example, AUTION EYE® AI-4510 (manufactured by Arkray, Inc.).

By detecting the presence of erythrocytes in a sample derived from a subject, or by the result of counting the number of erythrocytes in the sample derived from the subject, it is possible to suspect the presence of a disease such as nephritis, and to determine a treatment plan (for example, the administration of a drug) for such a disease, as necessary.

EXAMPLES

Examples are described for the purpose of disclosure, and are not intended to limit the scope of the present disclosure.

Example 1

At room temperature, polyoxyethylene (20) sorbitan monolaurate (Tween® 20; manufactured by FUJIFILM Wako Pure Chemical Corporation) having a final concentration of 0.01% was added to PBS (pH 7.4) (27575-31, manufactured by Nakalai Tesque, Inc.) (lx concentration), and the mixture was stirred. To the resulting solution, NH-RAS06 (manufactured by Nikko Rica Corporation) (final concentration: $1.0 \times 10^{-4}$ mg/mL), which is a raspberry-like, alumina microparticle-encapsulated silicone powder having an average particle size of 6 μm, was added, and then the resulting mixture was sufficiently mixed by inversion, to prepare Sample 1. Further, a pooled urine (reference sample) containing immobilized erythrocytes was prepared by the method disclosed in Non-patent Document 1.

Figure 2:
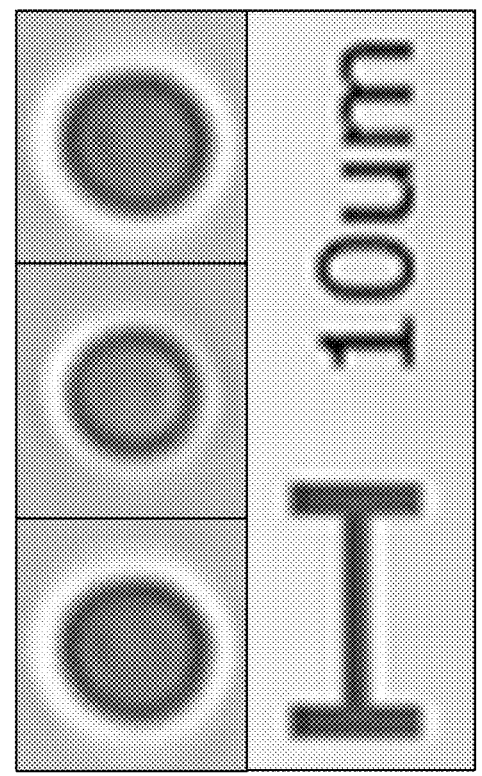
FIG. 2 shows images (photographs) illustrating the form of immobilized erythrocytes contained in a reference sample, captured by the urine sediment analyzer.

Using a urine sediment analyzer, AUTION EYE® AI-4510 (manufactured by Arkray, Inc.), the powder particles of NH-RAS06 contained in Sample 1 and particles contained in the reference sample were imaged, to obtain the images of NH-RAS06 and of the immobilized erythrocytes. By observing the images of the particles of NH-RAS06 and the immobilized erythrocytes, it was determined whether or not the form and the particle size of the particles of NH-RAS06 contained in Sample 1 are similar to those of the immobilized erythrocytes contained in the reference sample. The images (photographs) of the particles of NH-RAS06 contained in Sample 1 are shown in FIG. 1, and the images (photographs) of the immobilized erythrocytes contained in the reference sample are shown in FIG. 2. As can be seen from the images shown in FIG. 1 and FIG. 2, both the particles of NH-RAS06 and the immobilized erythrocytes have a spherical form, and the condition of the particles of NH-RAS06 was extremely similar to that of the cytoplasm of the immobilized erythrocytes. Further, 90% or more of the particles of NH-RAS06 contained in Sample 1 were automatically identified as "erythrocytes".

Figure 3:
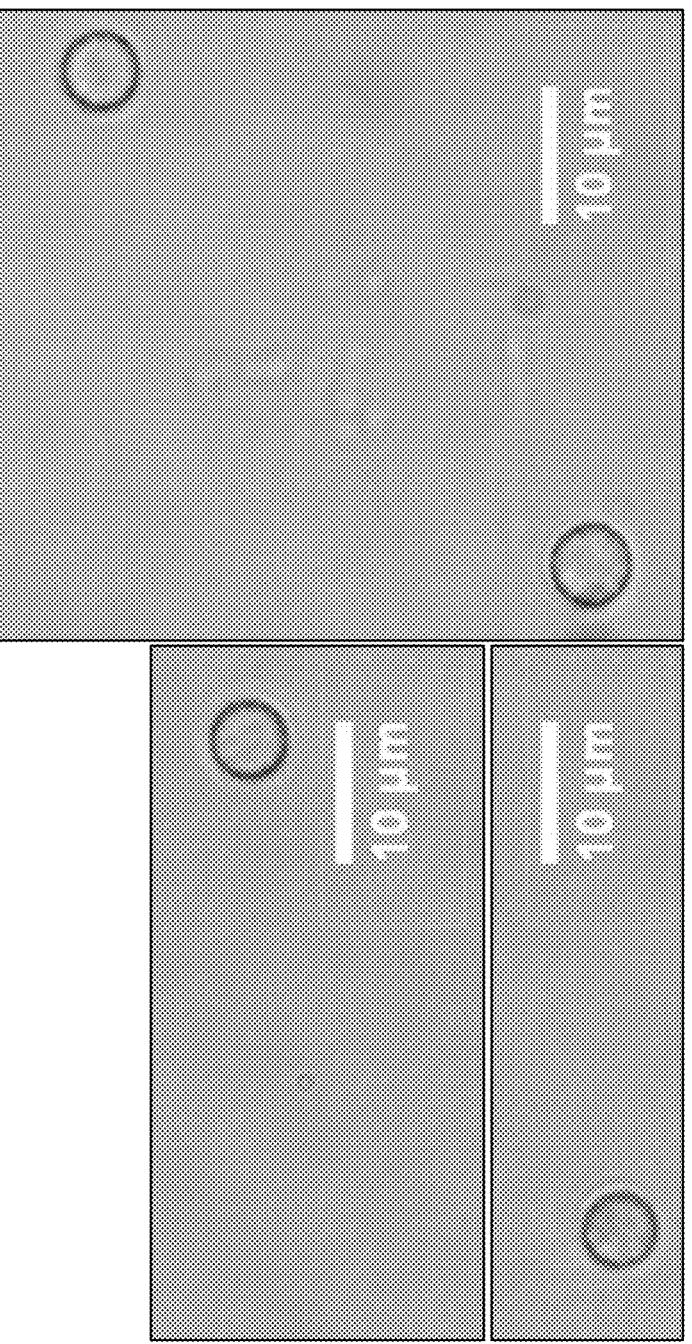
FIG. 3 shows images (photographs) illustrating the form of the particles of NH-RAS06 contained in Sample 1, obtained by observation with a biological microscope.
Figure 4:
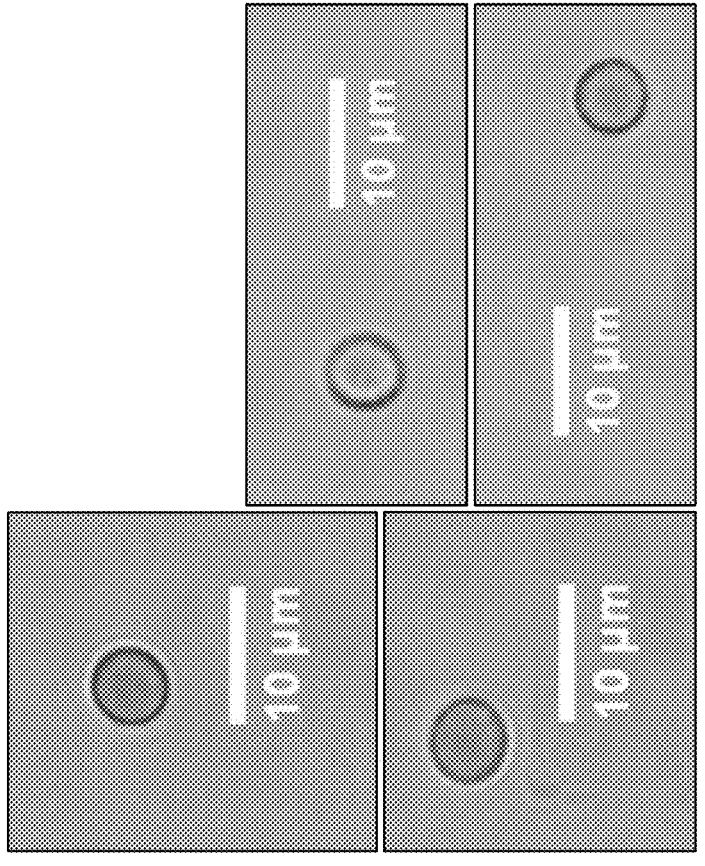
FIG. 4 shows images (photographs) illustrating the form of immobilized erythrocytes contained in the reference sample, obtained by observation with the biological microscope.

Using a biological microscope BX-2700TL (manufactured by WRAYMVER Inc.) in HPF mode (magnification: 400 times), the particles of NH-RAS06 contained in Sample 1 and the immobilized erythrocytes contained in the reference sample were observed, to determine whether or not the forms and the particle sizes of both are similar to each other. The images (photographs) of the particles of NH-RAS06 contained in Sample 1 are shown in FIG. 3, and the images (photographs) of the immobilized erythrocytes contained in the reference sample are shown in FIG. 4. As can be seen from the images shown in FIG. 3 and FIG. 4, the form, the particle size and the condition of the particles of NH-RAS06 were extremely similar to those of the immobilized erythrocytes, also in the observation with the biological microscope.

Example 2

The same procedure as in Example 1 was carried out except that Twinone SS-1000 (manufactured by CQV Co., Ltd.) (final concentration: $1.0 \times 10^{-4}$ mg/mL), which is golf ball-like amphipathic silicone beads having an average particle size of from 2 μm to 5 μm, was used instead of NH-RAS06 used in Example 1, to prepare Sample 2.

Figure 5:
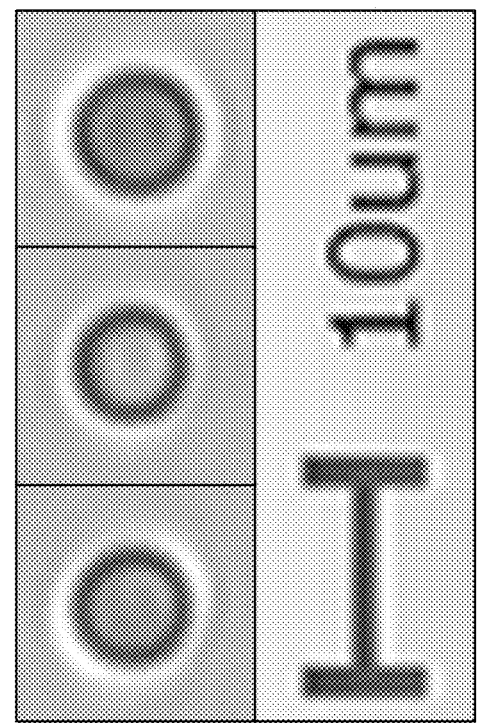
FIG. 5 shows images (photographs) illustrating the form of the particles of Twinone SS-1000 contained in Sample 2, captured by the urine sediment analyzer.

Using AUTION EYE® AI-4510, the bead particles of Twinone SS-1000 contained in Sample 2 were imaged, and the evaluation of Twinone SS-1000 was carried out, in the same manner as in Example 1. The images (photographs) of the particles of Twinone SS-1000 contained in Sample 2 are shown in FIG. 5. As can be seen from the images shown in FIG. 5, the form, the particle size and the condition of the particles of Twinone SS-1000 were extremely similar to those of the immobilized erythrocytes, as in the case of NH-RAS06 in Example 1. Further, the particles included in Twinone SS-1000 were automatically identified as erythrocytes by the urine sediment analyzer.

Figure 6:
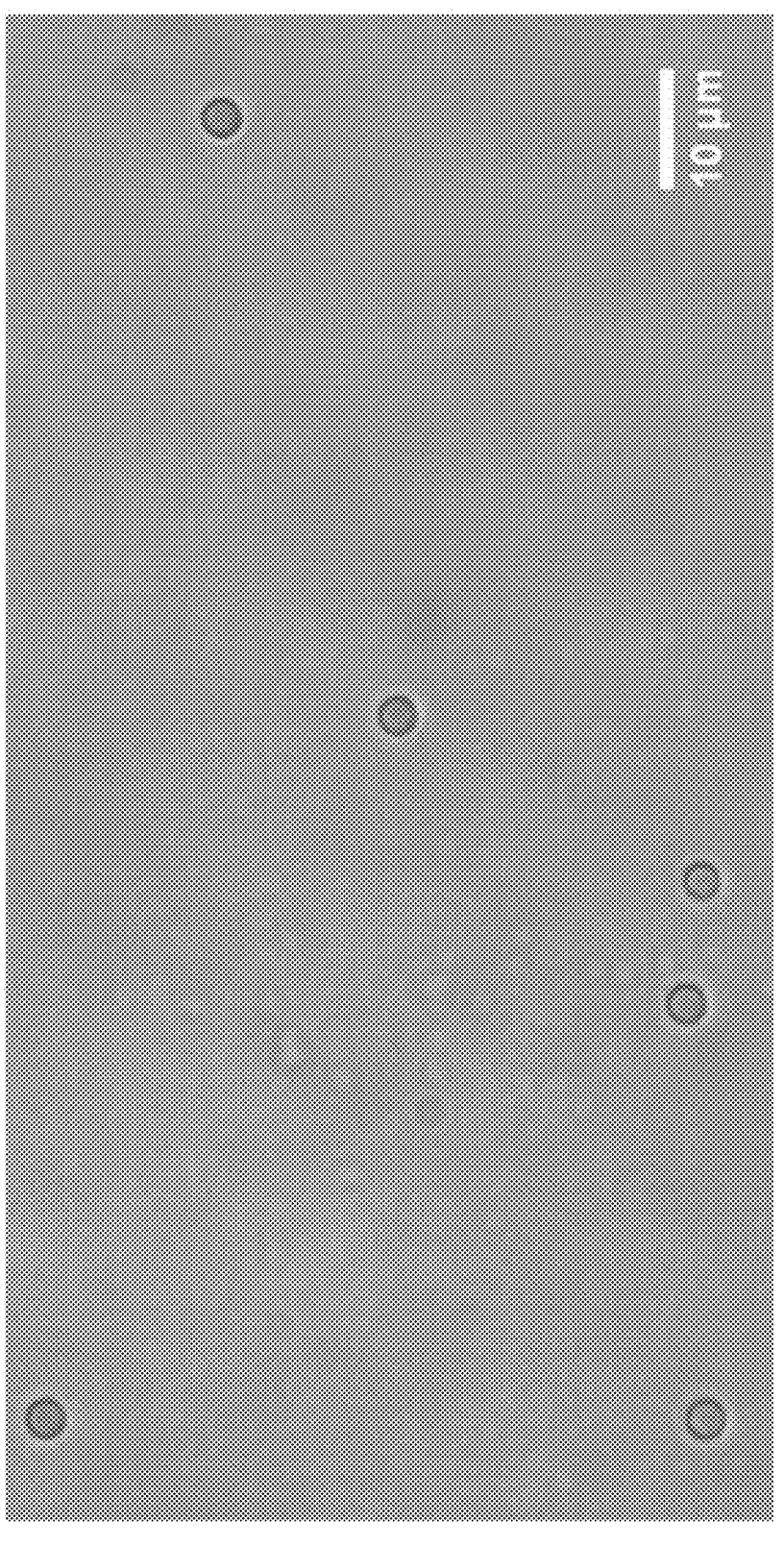
FIG. 6 shows an image (photograph) illustrating the form of the particles of Twinone SS-1000 contained in Sample 2, obtained by observation with the biological microscope.

Using the BX-2700TL in HPF mode (magnification: 400 times), the bead particles of Twinone SS-1000 contained in Sample 2 were observed. The image (photograph) of the particles of Twinone SS-1000 contained in Sample 2 is shown in FIG. 6. As can be seen from the image shown in FIG. 6, the form, the particle size and the condition of the particles of Twinone SS-1000 were extremely similar to those of the immobilized erythrocytes, also in the observation with the biological microscope.

Comparative Example 1

The same procedure as in Example 1 was carried out except that Viscopearl® D-10 (manufactured by Rengo Co., Ltd.) (final concentration: $5.0 \times 10^{-4}$ mg/mL), which is spherical cellulose particles having an average particle size of 10 μm, was used instead of NH-RAS06 used in Example 1, to prepare Sample 3.

Figure 7:
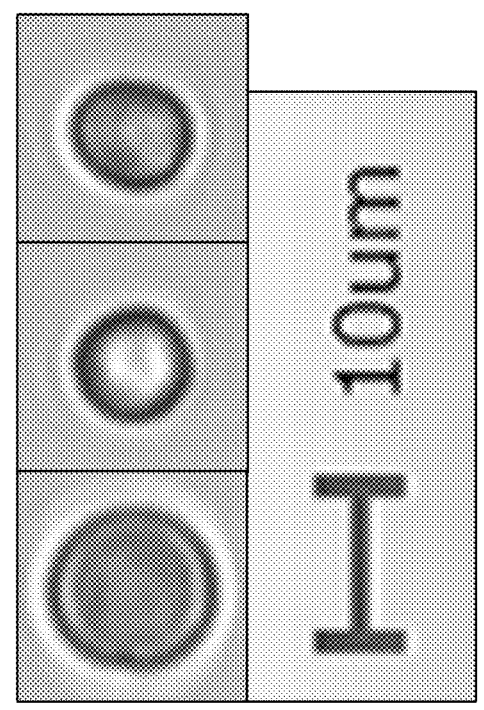
FIG. 7 shows images (photographs) illustrating the form of the particles of Viscopearl® D-10 contained in Sample 3, captured by the urine sediment analyzer.

Using AUTION EYE® AI-4510, the particles of Viscopearl® D-10 contained in Sample 3 were imaged, and the evaluation of Viscopearl® D-10 was carried out, in the same manner as in Example 1. The images (photographs) of the particles of Viscopearl® D-10 contained in Sample 3 are shown in FIG. 7. As can be seen from the images shown in FIG. 7, the particles of Viscopearl® D-10 have a distorted spherical form and a non-uniform particle size, and the condition of the cytoplasm of the immobilized erythrocytes could not be confirmed, as well; therefore, it was determined that the particles are not similar to the immobilized erythrocytes.

Comparative Example 2

The same procedure as in Example 1 was carried out except that Viscopearl® D-5 (manufactured by Rengo Co., Ltd.) (final concentration: $5.0 \times 10^{-4}$ mg/mL), which is spherical cellulose particles having an average particle size of 5 μm, was used instead of NH-RAS06 used in Example 1, to prepare Sample 4.

Figure 8:
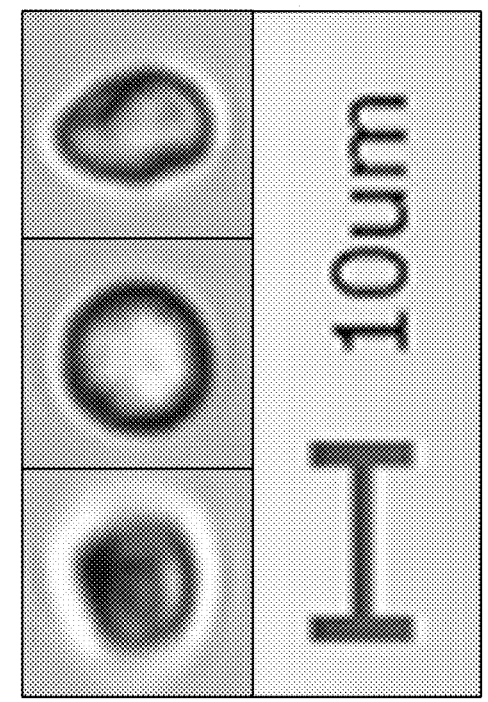
FIG. 8 shows images (photographs) illustrating the form of the particles of Viscopearl® D-5 contained in Sample 4, captured by the urine sediment analyzer.

Using AUTION EYE® AI-4510, the particles of Viscopearl® D-5 contained in Sample 4 were imaged, and the evaluation of Viscopearl® D-5 was carried out, in the same manner as in Example 1. The images (photographs) of the particles of Viscopearl® D-5 contained in Sample 4 are shown in FIG. 8. As can be seen from the images shown in FIG. 8, the particles of Viscopearl® D-5 have a distorted spherical form and a non-uniform particle size, and the condition of the cytoplasm of the immobilized erythrocytes could not be confirmed, as well; therefore, it was determined that the particles are not similar to the immobilized erythrocytes.

Comparative Example 3

The same procedure as in Example 1 was carried out except that KCX-5000 (manufactured by Dainichiseika Color & Chemicals Mfg. Co., Ltd.) (final concentration: $5.0 \times 10^{-4}$ mg/mL), which is cellulose particles having an average particle size of 11 μm, was used instead of NH-RAS06 used in Example 1, to prepare Sample 5.

Figure 9:
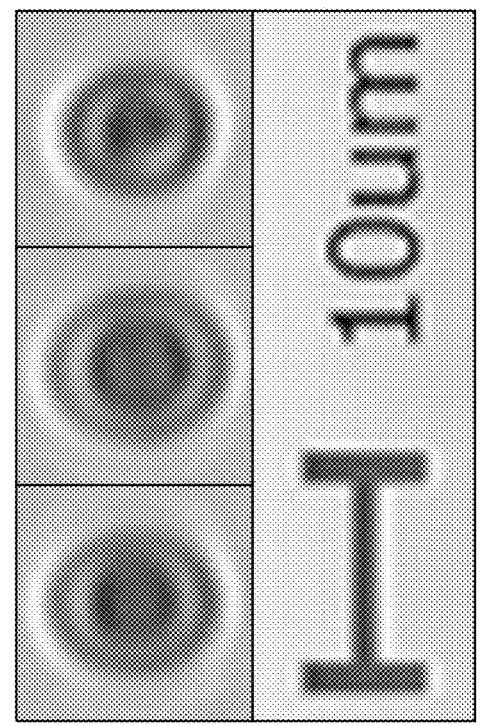
FIG. 9 shows images (photographs) illustrating the form of the particles of KCX-5000 contained in Sample 5, captured by the urine sediment analyzer.

Using AUTION EYE® AI-4510, the particles of KCX-5000 contained in Sample 5 were imaged, and the evaluation of KCX-5000 was carried out, in the same manner as in Example 1. The images (photographs) of the particles of KCX-5000 contained in Sample 5 are shown in FIG. 9. As can be seen from the images shown in FIG. 9, the particles of KCX-5000 have a spherical form and a particle size about the same as that of the immobilized erythrocytes, but the condition of the cytoplasm of the immobilized erythrocytes could not be confirmed; therefore, it was determined that the particles are not similar to the immobilized erythrocytes.

Comparative Example 4

The same procedure as in Example 1 was carried out except that MX-1000 (manufactured by Soken Kagaku Co., Ltd.) (final concentration: $8.0 \times 10^{-1}$ mg/mL), which is cross-linked acrylic monodispersed particles having an average particle size of 10 μm, was used instead of NH-RAS06 used in Example 1, to prepare Sample 6.

Figure 10:
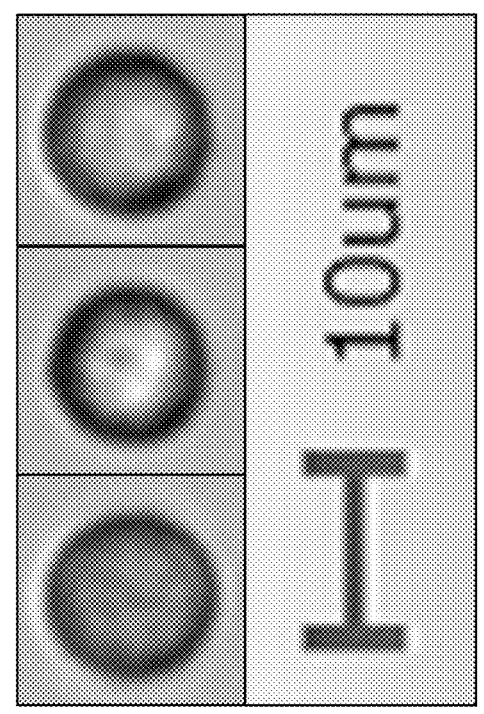
FIG. 10 shows images (photographs) illustrating the form of the particles of MX-1000 contained in Sample 6, captured by the urine sediment analyzer.

Using AUTION EYE® AI-4510, the particles of MX-1000 contained in Sample 6 were imaged, and the evaluation of MX-1000 was carried out, in the same manner as in Example 1. The images (photographs) of the particles of MX-1000 contained in Sample 6 are shown in FIG. 10. As can be seen from the images shown in FIG. 10, the particles of MX-1000 have a spherical form, but the condition of the cytoplasm of the immobilized erythrocytes could not be confirmed, because the images tend to have a white blurred core or an emphasized contour; therefore, it was determined that the particles are not similar to the immobilized erythrocytes.

Comparative Example 5

The same procedure as in Example 1 was carried out except that Techpolymer® BIO EF-C (manufactured by Sekisui Kasei Co., Ltd.) (final concentration: $5.0 \times 10^{-4}$ mg/mL), which is cross-linked polymer microparticles having an average particle size of 8.15 µm, was used instead of NH-RAS06 used in Example 1, to prepare sample 7.

Figure 11:
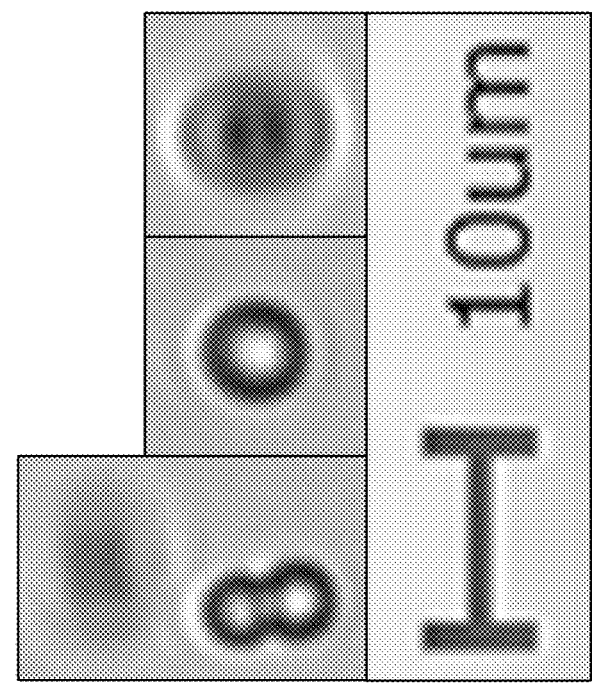
FIG. 11 shows images (photographs) illustrating the form of the particles of Techpolymer® BIO EF-C contained in Sample 7, captured by the urine sediment analyzer.

Using AUTION EYE® AI-4510, the particles of Techpolymer® BIO EF-C contained in Sample 7 were imaged, and the evaluation of Techpolymer® BIO EF-C was carried out, in the same manner as in Example 1. The images (photographs) of the particles of Techpolymer® BIO EF-C contained in Sample 7 are shown in FIG. 11. As can be seen from the images shown in FIG. 11, the particles of Techpolymer® BIO EF-C have a spherical form but have a particle size smaller than that of the immobilized erythrocytes, and the condition of the cytoplasm of the immobilized erythrocytes could not be confirmed, as well; therefore, it was determined that the particles are not similar to the immobilized erythrocytes.

Comparative Example 6

The same procedure as in Example 1 was carried out except that NIKKALYCO® AS-100SG (manufactured by Nikka Limited) (final concentration: $5.0 \times 10^{-4}$ mg/mL), which is starch particles having an average particle size of 17 µm, was used instead of NH-RAS06 used in Example 1, to prepare Sample 8.

Figure 12:
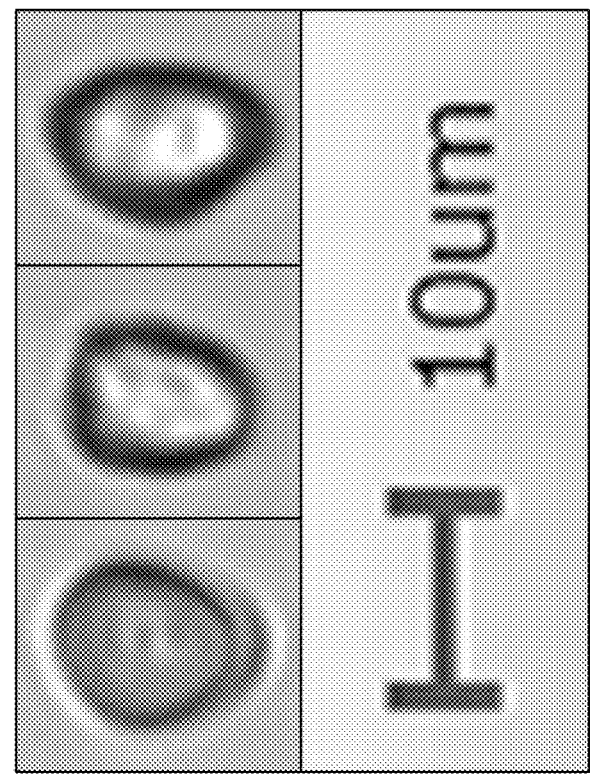
FIG. 12 shows images (photographs) illustrating the form of the particles of NIKKALYCO® AS-100SG contained in Sample 8, captured by the urine sediment analyzer.

Using AUTION EYE® AI-4510, the particles of NIK-KALYCO® AS-100SG contained in Sample 8 were imaged, and the evaluation of NIKKALYCO® AS-100SG was carried out, in the same manner as in Example 1. The images (photographs) of the particles of NIKKALYCO® AS-100SG contained in Sample 8 are shown in FIG. 12. As can be seen from the images shown in FIG. 12, the particles of NIKKALYCO® AS-100SG, which were automatically identified as erythrocytes, have a distorted spherical form, have a particle size larger than that of the immobilized erythrocytes, and the condition of the cytoplasm of the immobilized erythrocyte could not be confirmed, as well; therefore, it was determined that the particles are not similar to the immobilized erythrocytes.

Comparative Example 7

The same procedure as in Example 1 was carried out except that Techpolymer® BIO EF-B (manufactured by Sekisui Kasei Co., Ltd.) (final concentration: $5.0 \times 10^{-4}$ mg/mL), which is polymer microparticles having an average particle size of 10 µm, was used instead of NH-RAS06 used in Example 1, to prepare Sample 9.

Figure 13:
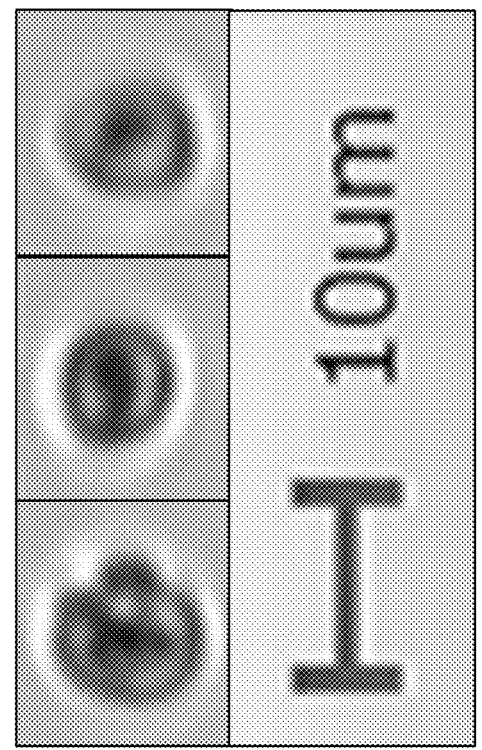
FIG. 13 shows images (photographs) illustrating the form of the particles of Techpolymer® BIO EF-B contained in Sample 9, captured by the urine sediment analyzer.

Using AUTION EYE® AI-4510, the particles of Techpolymer® BIO EF-B contained in Sample 9 were imaged, and the evaluation of Techpolymer® BIO EF-B was carried out, in the same manner as in Example 1. The images (photographs) of the particles of Techpolymer® BIO EF-B contained in Sample 9 are shown in FIG. 13. As can be seen from the images shown in FIG. 13, the particles of Techpolymer® BIO EF-B have a distorted spherical form, and the condition of the cytoplasm of the immobilized erythrocytes could not be confirmed, as well; because the particles appear blackish overall; therefore, it was determined that the particles are not similar to the immobilized erythrocytes.

While the invention has been described in detail with reference to exemplary embodiments thereof, it will be apparent to one skilled in the art that various changes may be made, and equivalents employed, without departing from the scope of the invention. Each of the aforementioned documents as well as JP2022-148425 is incorporated by reference herein in its entirety.

What is claimed is:

1. A method for analyzing a sample using a urine sediment analyzer, comprising the steps of:
controlling measurement accuracy of the urine sediment analyzer with artificial particles whose form as observed with a microscope is similar to the form of erythrocytes as observed therewith, for measuring a concentration of erythrocytes in the sample; and
analyzing the sample with the urine sediment analyzer,
wherein the artificial particles are made of polymethylsilsesquioxane, wherein the artificial particles have an average particle size of from 2 µm to 6 µm, and wherein the artificial particles have a golf ball-like form or a raspberry-like form.

2. The method according to claim 1, wherein the color of the artificial particles as observed with the microscope is similar to the color of the erythrocytes as observed therewith.

3. The method according to claim 1, wherein the artificial particles are artificial particles included in at least one of raspberry-like, alumina microparticle-encapsulated polymethylsilsesquioxane particles or golf ball-like polymethylsilsesquioxane particles.

4. A method for controlling a measurement accuracy of an analyzer that measures a concentration of particles whose form is similar to the form of erythrocytes in a sample, by counting the number of the particles in the sample, the method comprising the steps of:
measuring a concentration of particles in a quality control substance comprising artificial particles whose form is similar to the form of erythrocytes, using the analyzer, to obtain a measured value; and
determining the measurement accuracy of the analyzer by comparing the measured value with a reference value,
wherein the artificial particles are made of polymethylsilsesquioxane, wherein the artificial particles have an average particle size of from 2 µm to 6 µm, and wherein the artificial particles have a golf ball-like form or a raspberry-like form.

5. The method according to claim 4, wherein the color of the artificial particles as observed with a microscope is similar to the color of the erythrocytes as observed therewith.

6. The method according to claim 4, wherein the artificial particles are artificial particles included in at least one of raspberry-like, alumina microparticle-encapsulated polymethylsilsesquioxane particles or golf ball-like polymethylsilsesquioxane particles.

* * * * *